US007481832B1

(12) United States Patent
Meridew et al.

(10) Patent No.: US 7,481,832 B1
(45) Date of Patent: Jan. 27, 2009

(54) METHOD AND APPARATUS FOR USE OF A SELF-TAPPING RESORBABLE SCREW

(75) Inventors: Jason D Meridew, Columbia City, IN (US); Troy Walters, Plymouth, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 342 days.

(21) Appl. No.: 10/657,940

(22) Filed: Sep. 9, 2003

(51) Int. Cl.
  *A61B 17/86* (2006.01)
  *A61B 17/064* (2006.01)
  *A61F 2/08* (2006.01)
(52) U.S. Cl. ............... 606/319; 606/75; 606/232
(58) Field of Classification Search ............... 606/72, 606/73, 75, 232, 66, 151–158; 411/417–419, 411/321, 322, 921; 623/13.13, 13.14
See application file for complete search history.

(56) References Cited

U.S. PATENT DOCUMENTS

| | | | |
|---|---|---|---|
| 2,787,010 A | 4/1957 | Uphoff | |
| 3,869,741 A | 3/1975 | Logan | |
| 4,432,358 A * | 2/1984 | Fixel | 606/66 |
| 4,570,623 A | 2/1986 | Ellison et al. | |
| 5,038,589 A * | 8/1991 | Martin | 70/368 |
| 5,352,229 A | 10/1994 | Goble et al. | |
| 5,354,299 A * | 10/1994 | Coleman | 606/73 |
| 5,425,490 A * | 6/1995 | Goble et al. | 227/175.1 |
| 5,584,835 A | 12/1996 | Greenfield | |
| 5,620,323 A * | 4/1997 | Bressman et al. | 433/174 |
| 5,733,307 A | 3/1998 | Dinsdale | |
| 5,897,593 A * | 4/1999 | Kohrs et al. | 623/17.16 |
| 5,931,869 A | 8/1999 | Boucher et al. | |
| 6,120,503 A * | 9/2000 | Michelson | 606/61 |
| 6,224,631 B1 * | 5/2001 | Kohrs | 623/17.11 |
| 6,241,770 B1 * | 6/2001 | Michelson | 623/17.11 |
| 6,280,472 B1 | 8/2001 | Boucher et al. | |
| 6,402,757 B1 | 6/2002 | Moore, III et al. | |
| 6,413,259 B1 | 7/2002 | Lyons et al. | |
| 6,666,877 B2 * | 12/2003 | Morgan et al. | 606/232 |
| 6,835,206 B2 * | 12/2004 | Jackson | 623/17.11 |
| 6,840,953 B2 * | 1/2005 | Martinek | 606/232 |
| 2002/0004660 A1 | 1/2002 | Henniges et al. | |

* cited by examiner

*Primary Examiner*—Eduardo C Robert
*Assistant Examiner*—Richard Shaffer
(74) *Attorney, Agent, or Firm*—Harness, Dickey & Pierce, P.L.C.

(57) ABSTRACT

A bone attachment apparatus and implantation system. The attachment device provides a screw with channels formed therein for implantation within a bone aperture. The channels are used as a torque transfer surface during implantation, and cooperate with a thread forming tap to enable screw implantation simultaneously with thread formation within the aperture. The tap can be used to form channels within the bone. A staple is coupled to the screw and the bone, utilizing the respective channels formed therein, to prevent rotation therebetween. The screw can also cooperate with the staple to secure a soft tissue graft.

32 Claims, 9 Drawing Sheets

METHOD AND APPARATUS FOR USE OF A SELF-TAPPING RESORBABLE SCREW

FIELD OF THE INVENTION

The present invention is generally related to a bone attachment device and, more particularly, to a method and apparatus for implanting a self-tapping resorbable bone screw with locking and soft tissue graft securing features.

BACKGROUND OF THE INVENTION

Modern medical techniques include suturing soft tissue to bone and repair of bone during, for example, reconstructive surgery. In one form these techniques involve attaching a suture to a bone screw, or anchor, installing the bone screw into the bone and connecting the soft tissue to the bone via the suture. One drawback associated with prior art bone screws is the potential for a bone screw to back out after implantation. To inhibit back out, bone screws have been modified with various thread designs and locking features, with some success.

These bone screws can also be used for repair of bone by inserting the screw into a prepared bone aperture. The screw can be used to attach bone to bone or to attach a reconstruction plate or other prosthesis to a bone. Most of these techniques can benefit from the use of a resorbable screw with a self-locking feature. When installing a bone anchor or screw, a surgeon will typically tap a hole, remove the tap and then install the screw into the hole while maintaining the alignment of the bone with another bone or a prosthesis. Therefore, what is needed is an implantation system for a bone screw utilizing a self-tapping resorbable screw with a soft tissue attachment and locking features for repair of bone or soft tissue graft attachment.

SUMMARY OF THE INVENTION

In accordance with the teachings of the present invention, a method and apparatus for a self-tapping resorbable bone screw system and locking feature to secure a soft tissue graft is disclosed. In one form, the present invention provides a channeled screw having a generally cylindrical body, a threaded outer surface and a channel defining an interior locking surface and a tap that is configured to fit within the channel such that the channel screw can be threaded into a bone aperture as the tap forms threads within the bone aperture.

In another form, the present invention provides a method of installing a bone anchor to a bone wherein a bone screw and tap are threaded into a bone aperture and the tap is removed forming a longitudinal slot within the bone aperture and a staple is inserted into the slot. The staple can then be used to lock the bone screw in place and prevent relative rotation between the bone screw and the bone and also the staple can be used to secure a soft tissue graft.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the embodiments of a method and apparatus for implantation of a bone screw are merely exemplary in nature and are in no way intended to limit the invention, its application, or uses. Moreover, while the present invention is described in detail with reference to a resorbable polymer bone screw, it will be appreciated by those skilled in the art that the present invention is not limited to a resorbable polymer but the bone screw may also be formed using any other resorbable or biocompatible material, such as allograft, ceramics, ceramic-polymer mixtures, or with non-resorbable materials such as titanium. It should also be appreciated that the staple may be formed of any suitable material that is capable of locking the bone screw and/or securing a bone graft.

Figure 1:
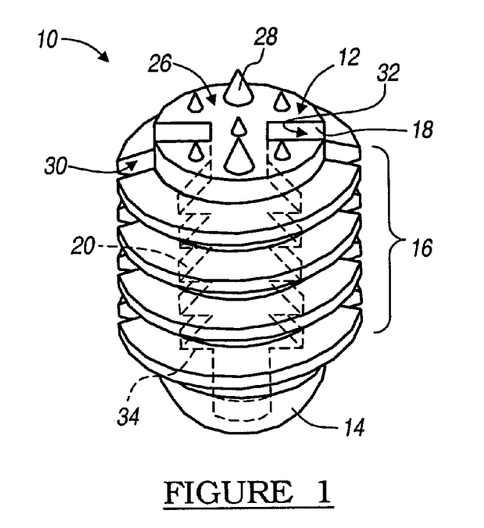
FIG. 1 is a perspective view of a bone screw in accordance with the teachings of the present invention.
Figure 2:
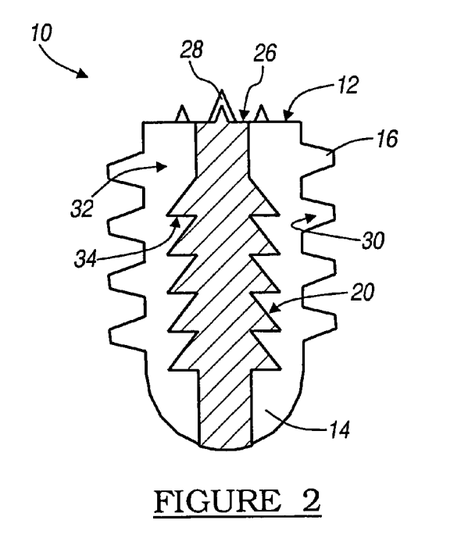
FIG. 2 is a sectional side view of the bone screw of FIG. 1.
Figure 3:
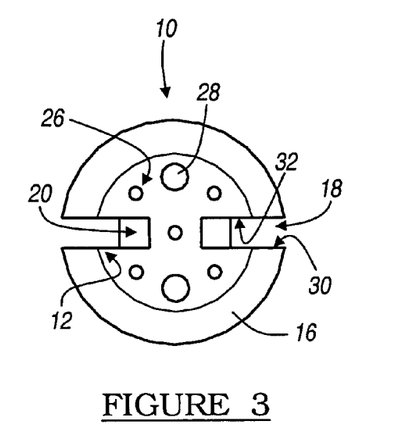
FIG. 3 is a top view of the bone screw of FIG. 1.

With specific reference to FIGS. 1-3, an implant, or bone screw, 10 is illustrated generally to be a channeled screw including a top surface 12, a bottom portion 14, a contoured portion 16 and screw channels 18 that define anchor locking surfaces 20. Top surface 12 includes a graft holding face 26 with spikes 28 extending therefrom. Graft holding face 26 and spikes 28 bindingly engages a material such as a soft tissue graft and will be discussed later in more detail. Contoured portion 16 is illustrated to define a threaded surface intersecting channels 18 to define threaded end surfaces 30. Channels 18 are formed within bone screw 10 to provide a torque surface 32 for implantation of bone screw 10, as discussed hereinafter. Anchor locking surfaces 20 include a series of resilient, downwardly facing surfaces 34.

Figure 4:
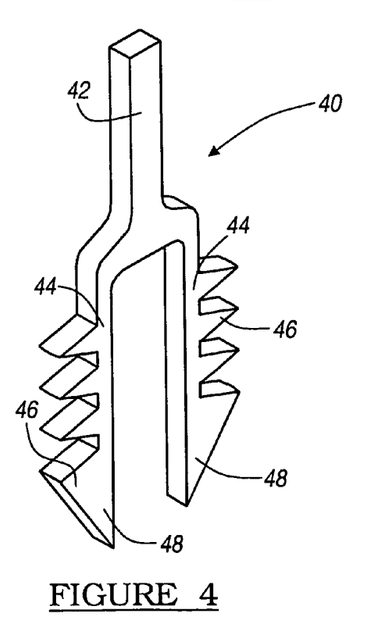
FIG. 4 is a bifurcated tap in accordance with the teachings of the present invention.

Referring now briefly to FIG. 4, a tap or driver 40 is illustrated to include a shaft 42, driving portions 44 defining linearly spaced cutting, or thread forming, portions 46 and alignment ends 48. Driving portions 44 are bifurcated with respect to shaft 42. Tap 40 is formed of titanium or of any suitable material for forming threads in a working surface, such as a bone, as described below. Thread forming portions 46 are illustrated to include a plurality of linearly spaced extensions configured to cut a predetermined surface within a work material, as detailed herein.

Figure 5:
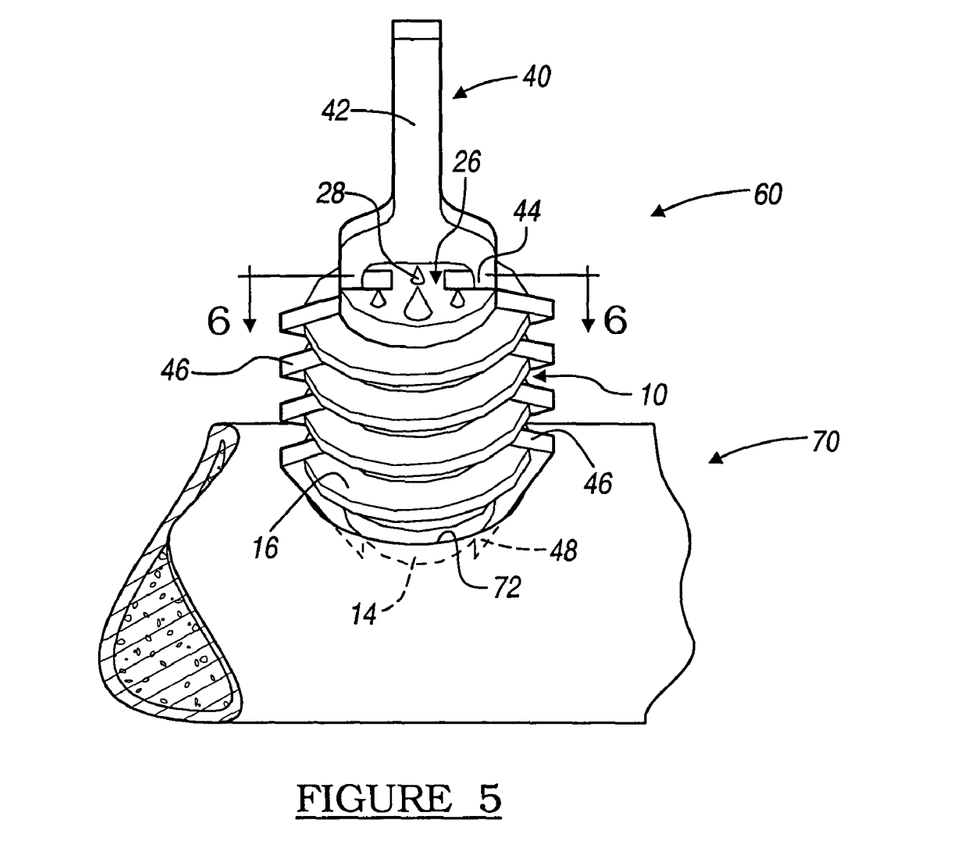
FIG. 5 is a perspective view of the tap of FIG. 4 installed within the bone screw of FIG. 1, forming a screw implantation system aligned with a bone aperture.
Figure 6:
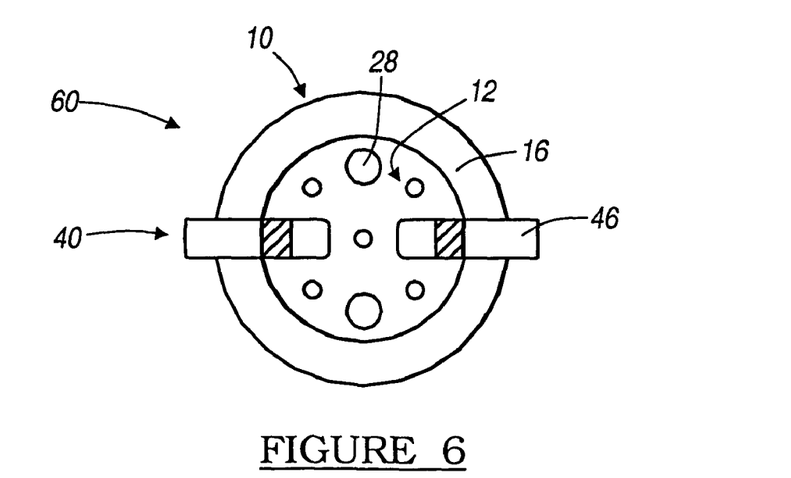
FIG. 6 is a sectional top view of the screw implantation system of FIG. 5 taken along the line 6-6.
Figure 7:
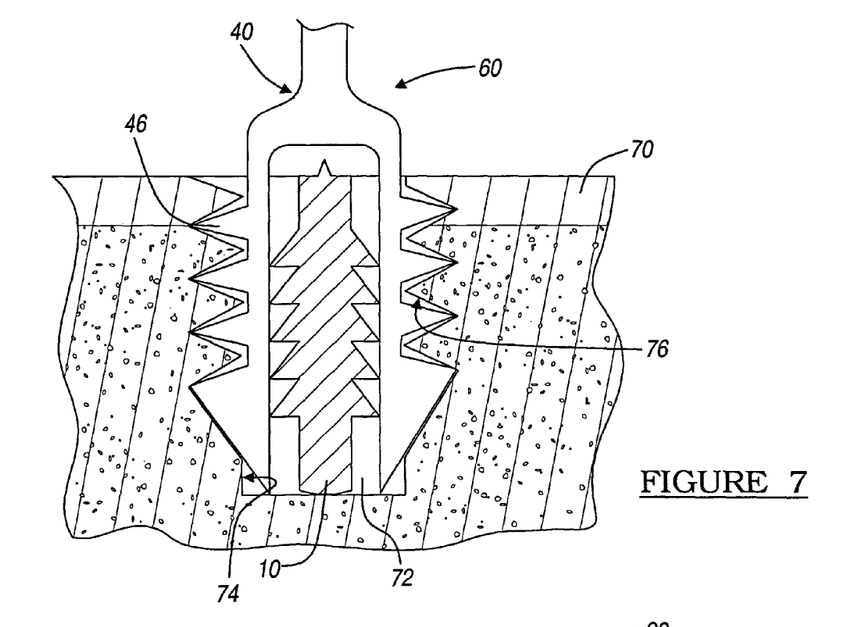
FIG. 7 is a side sectional view of the screw implantation system of FIG. 5 illustrating the system inserted within a bone aperture.

FIGS. 5-7 illustrate a screw implantation system 60 comprising the bone screw 10 and the tap or driver 40. Driving portions 44 of tap 40 are interposed within screw channels 18 of bone screw 10 such that thread forming portions 46 and threaded end surfaces 30 are generally aligned.

With specific reference to FIG. 7, screw implantation system 60 is illustrated with a work material such as a bone 70 to provide an environmental reference. Bone 70 includes a pre-drilled aperture 72 having a generally cylindrical interior surface 74.

With continued reference to FIG. 7, the implantation of bone screw 10 will be described. When a self tapping fastening system is desired, a surgeon prepares a bone 70 by drilling or otherwise forming an aperture 72 therein. Tap 40 with bone screw 10 engaged therein is inserted into aperture 72 until alignment ends 48 are in contact with bone 70. Rotation of shaft 42 of tap 40 causes thread forming portions 46 to engage interior surface 74 of bone 70 thereby forming an implant engaging surface 76 within bone 70. As implant engaging surface 76 is formed by tap 40, contoured portion 16 of bone screw 10 engages implant engaging surface 76. Further rotation of tap 40 causes bone screw 10 to fully engage within implant engaging surface 76 such that bone screw 10 is further threaded into aperture 72. Thus provided, tap 40 drives bone screw 10 into aperture 72 while simultaneously forming implant engaging surface 76. Contoured portion 16 mates with implant engaging surface 76 to retain implant 10 in bone 70. It would be appreciated that, while contoured portion 16 is illustrated as having a threaded surface, contoured portion 16 can be provided with any surface that engages with an implant engaging surface formed within bone 70. When bone screw 10 has been inserted into aperture 72 to a desired engagement or depth, tap 40 is pulled out of aperture 72 in a direction that is parallel to the axis of bone screw 10. As tap 40 is pulled, a slot 80 (as best seen in FIG. 13) is formed by each driving portion 44.

Figures 8, 9, 10:
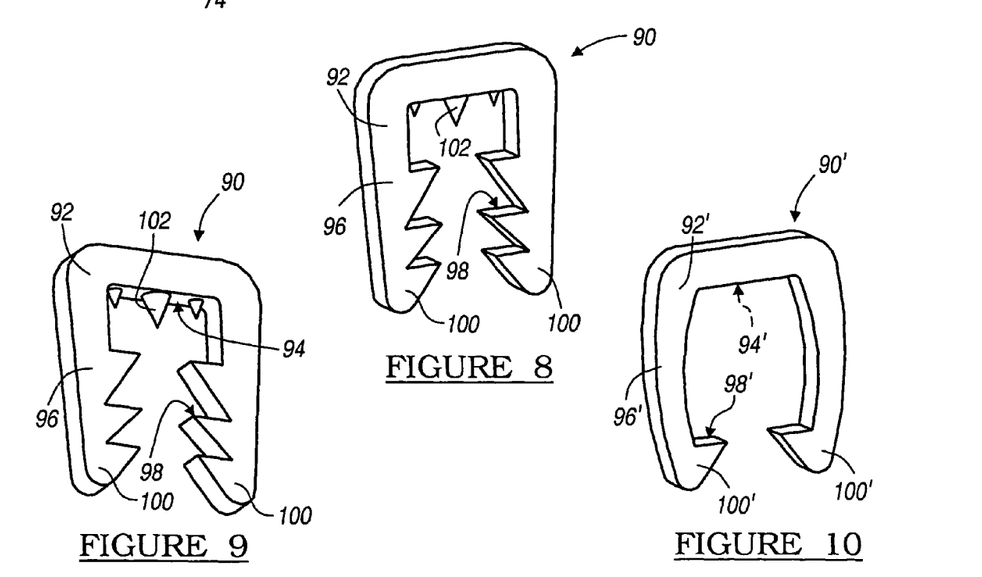
FIG. 8 is a perspective view of a staple in accordance with the teachings of the present invention.
FIG. 9 is a perspective view similar to FIG. 8, but taken from a different angle of view than of FIG. 8.
FIG. 10 is an alternate embodiment of a staple in accordance with the teachings of the present invention.

Referring now to FIGS. 8-9, a staple 90 is illustrated to include a top portion 92 defining a contoured, or graft holding surface, 94, legs 96 defining upward locking surfaces 98 and a bottom portion 100. Graft holding surface 94 is illustrated to include spikes 102 that are configured to bindingly engage a graft as described herein. Staple 90 may be constructed of titanium or stainless steel, or other biocompatible material.

Figure 11:
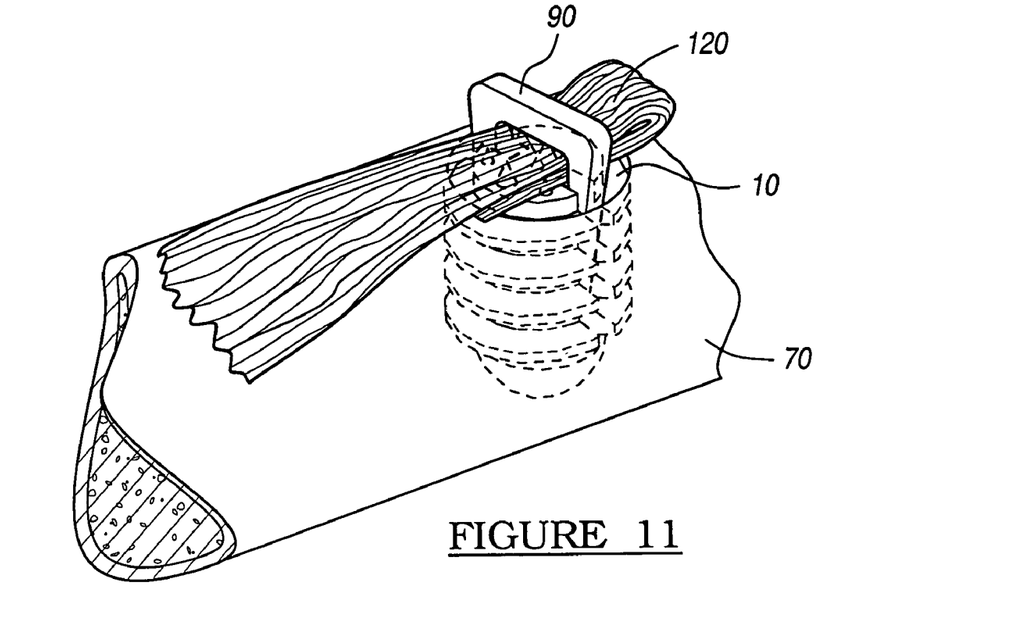
FIG. 11 is a perspective view of a bone screw in accordance with the teachings of the present invention installed within a bone and having a bone staple attached therein wherein a soft tissue graft is interposed therebetween.
Figure 12:
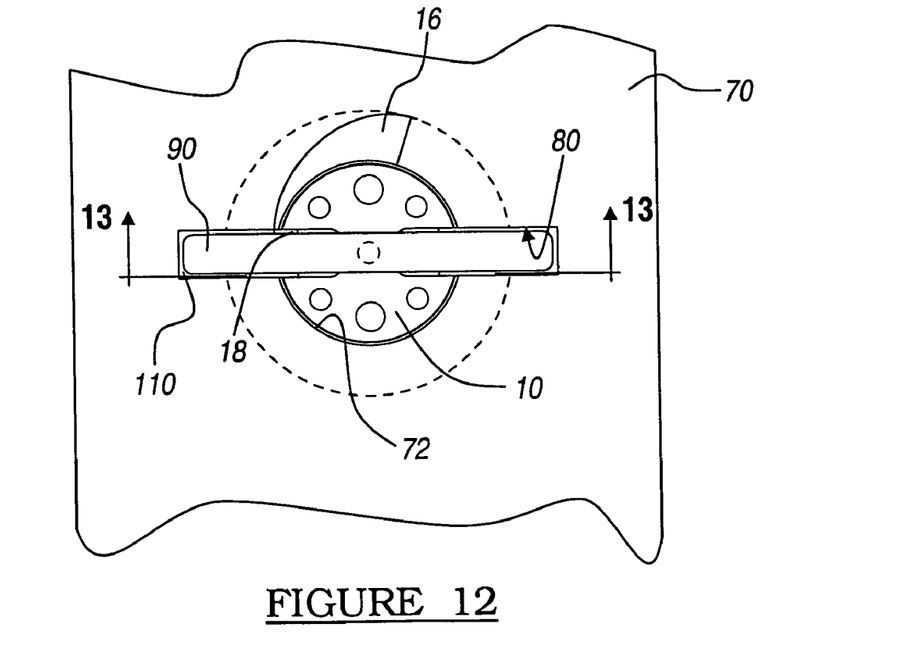
FIG. 12 is a top view of the bone screw of FIG. 11 with the soft tissue graft removed for clarity.
Figure 13:
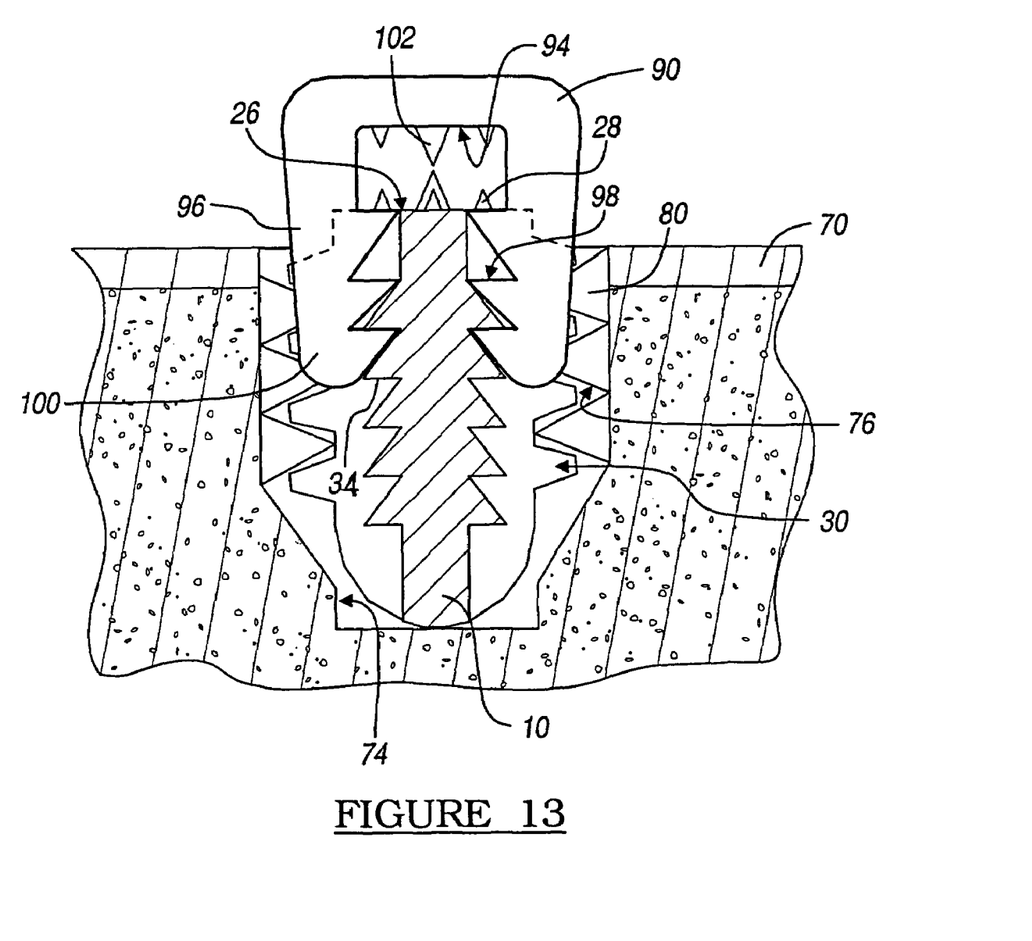
FIG. 13 is a side view of the bone screw of FIG. 12 taken along the line 13-13.

With reference now to FIGS. 11-13, additional features of bone screw 10 will now be described in detail. As best seen in FIGS. 12 and 13, bone screw 10 is implanted, or driven, into aperture 72 of bone 70. Slots 80 are formed within bone 70 as discussed above, and provide a pair of rectangular channels 110 that align with screw channels 18 of bone screw 10. Staple 90 is inserted into screw channels 18 and rectangular channels 110 until downwardly facing surfaces 34 engage with upward locking surfaces 98. Thus provided, staple 90 is locked within screw channels 18 and rectangular channels 110 such that bone screw 10 is inhibited from rotation relative to bone 70. Staple 90 can be further inserted into screw channels 18 and rectangular channels 110 to provide greater engagement depth and/or clearance.

An additional feature of bone screw 10 is illustrated in FIG. 11 wherein a soft tissue graft 120 is interposed between staple 90 and bone screw 10. In the embodiment shown, bottom portions 100 of staple 90 are inserted into screw channels 18 and rectangular channels 110 until upward locking surfaces 98 engage downwardly facing surfaces 34 and graft holding surface 94 bindingly secures graft 120 to graft holding face 26.

FIG. 10 illustrates an alternate embodiment of staple 90 in accordance with the teachings of the present invention as a staple 90'. Staple 90' includes a top portion 92' defining a surface 94', legs 96' defining upward locking surfaces 98' and a bottom portion 100. In the embodiment shown, staple 90' does not include spikes, and is intended for use as a screw locking member that couples to a bone screw 10 that does not include spikes 28. In this manner, staple 90' provides a low profile locking feature for bone screw 10.

Figure 14:
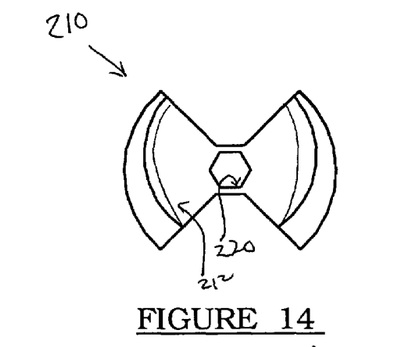
FIG. 14 is a top view of an alternate embodiment of the bone screw of FIG. 1, with the anchor locking surface removed for clarity.
Figure 15:
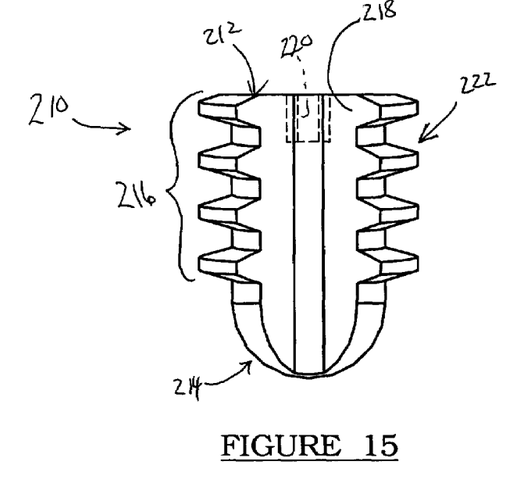
FIG. 15 is a side view of the bone screw of FIG. 14.
Figure 16:
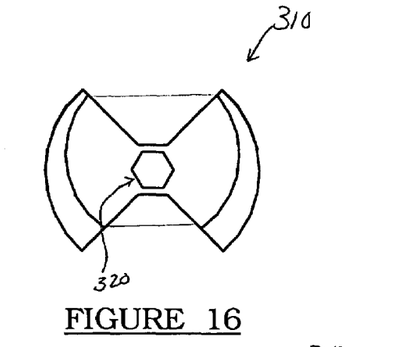
FIG. 16 is a top view of a further alternate embodiment of the bone screw of FIG. 1.
Figure 17:
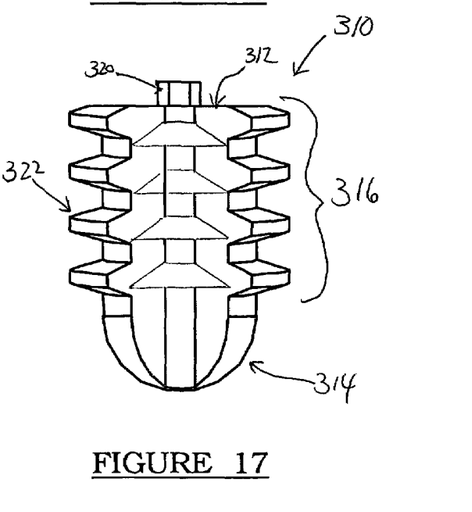
FIG. 17 is a side view of the bone screw of FIG. 15.

FIGS. 14-17 illustrate an alternate embodiment of the implant of the present invention wherein the implant is intended to be axially, or linerally, driven into a bone. FIGS. 14 and 15 illustrate an implant 210 having a top surface 212, a bottom portion 214, a contoured portion 216 and screw channels 218. The top surface 212 is illustrated to include a torque surface 220. While contoured portion 216 is illustrated in FIG. 15 as a series of annular protrusions 222, contoured portion 216 may also comprise a helical screw surface. FIGS. 16 and 17 illustrate an implant 310 having a top surface 312, a bottom portion 314, a contoured portion 316 and screw channels 318. The top surface 312 is illustrated to include a torque surface 320. While contoured portion 316 is illustrated in FIG. 17 as a series of annular protrusions 322, contoured portion 316 may also comprise a helical screw surface.

During implantation, the implant 210, 310 is attached to an impact driver. Implant 210, 310 is then driven or impacted into a bone, thereby forming a pair of slots within the bone as contoured surface 216 displaces a portion of the bone. The bone may be prepared with an aperture that is about of equivalent diameter to the bottom portion 214, 314 of implant 210, 310. As presently preferred, the implants 210 and 310 are constructed of a material that is capable of being driven into a bone without damage to the implant 210, 310. Implant 210, 310 is then rotated about 90 degrees to lock implant 210, 310 into the bone as contoured portion 216, 316 forms an implant engaging surface within the bone. Implant 210, 310 may be rotated by a tool attached to torque surface 220, 320. In a manner similar to implant 10, a staple may be inserted into the pair of slots formed into the bone to prevent rotation of implants 210, 310 to thereby lock the implant 210, 310 in place.

Figure 18:
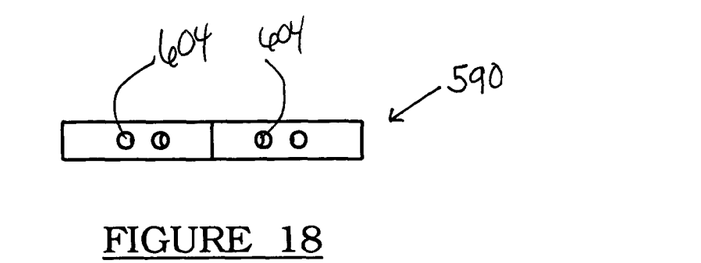
FIG. 18 is a top view of an alternate embodiment of the staple of FIG. 8.
Figure 19:
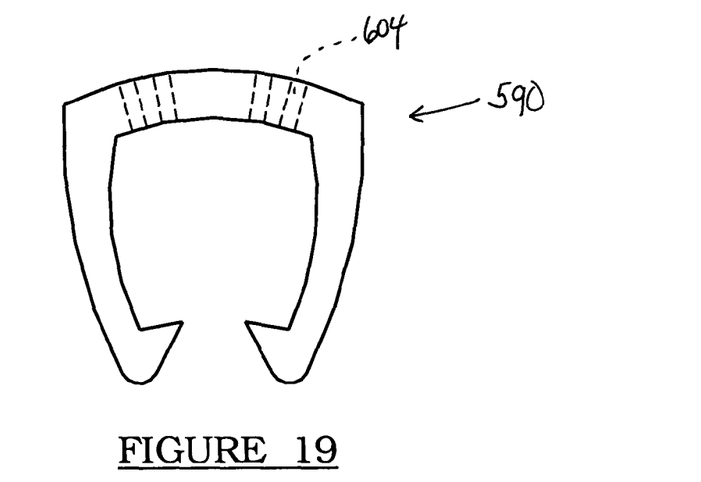
FIG. 19 is a side view of the staple of FIG. 18.
Figure 20:
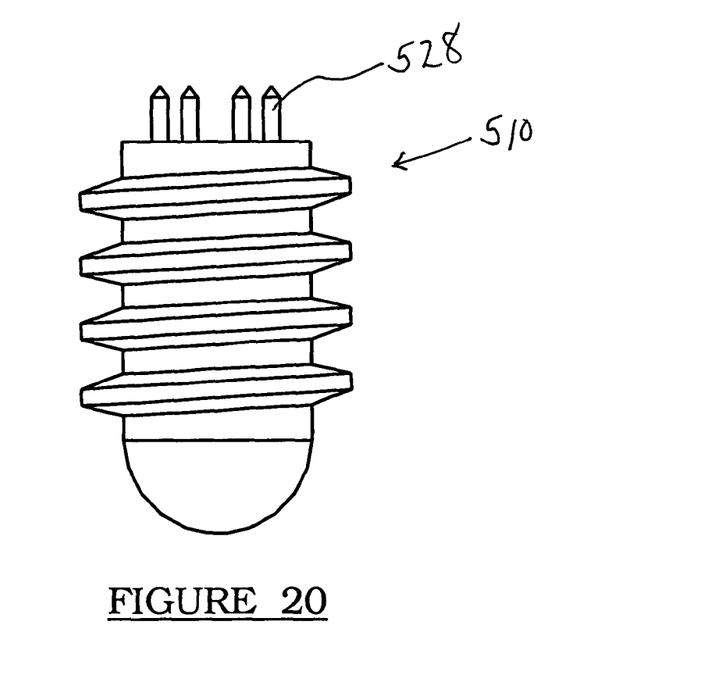
FIG. 20 side view of an alternate embodiment of the bone screw of FIG. 1, configured to attach to the staple of FIG. 18.

FIGS. 18-20 illustrate an alternate embodiment of the implant 10 and staple 90 of FIG. 13. As best seen in FIGS. 18 and 19, staple 590 includes graft apertures 604. FIG. 20 illustrates implant 510 to include graft pins 528. Graft pins 528 are configured to secure a graft between implant 510 and staple 590. Graft pins 528 are further configured to interpose within graft apertures 604 as staple 590 is attached to staple 510, thereby preventing the graft from detaching from graft pins 528.

Figure 21:
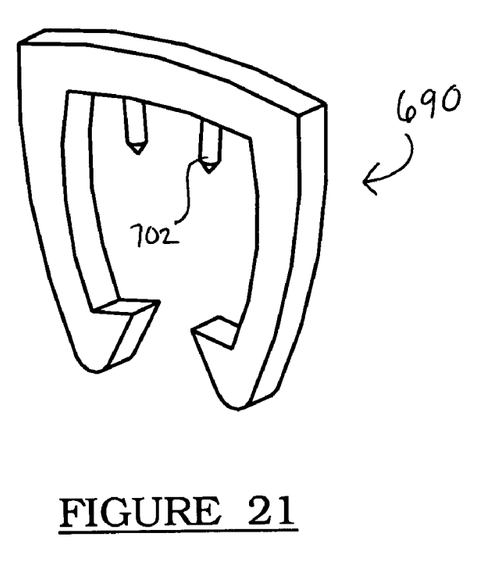
FIG. 21 a perspective view of a further alternate embodiment of the staple of FIG. 8.
Figure 22:
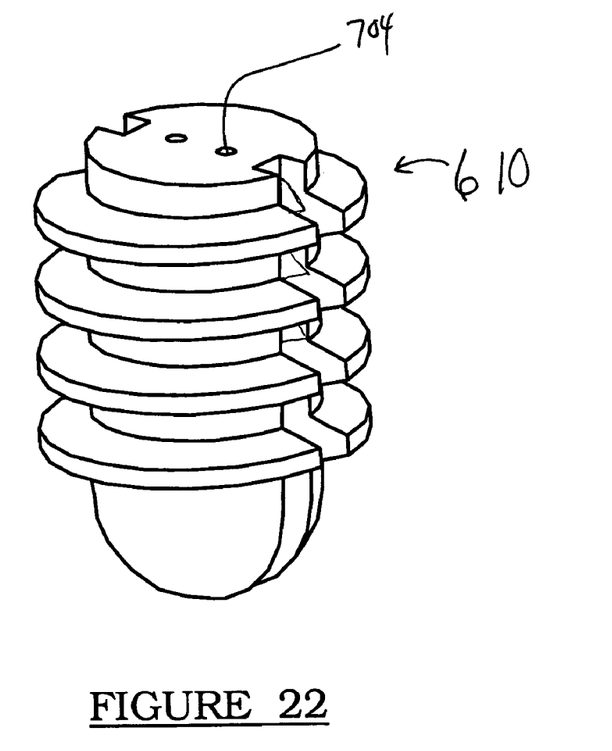
FIG. 22 side view of an alternate embodiment of the bone screw of FIG. 1, configured to attach to the staple of FIG. 21.

FIGS. 21-22 illustrate a further alternate embodiment of the implant 10 and staple 90 of FIG. 13. As best seen in FIG. 21, staple 690 includes graft pins 702. FIG. 22 illustrates implant 610 to include graft apertures 704. Graft pins 702 are configured to secure a graft between implant 610 and staple 590. Graft pins 702 are further configured to interpose within graft apertures 704 as staple 690 is attached to staple 610, thereby preventing the graft from detaching from graft pins 702.

Figure 23:
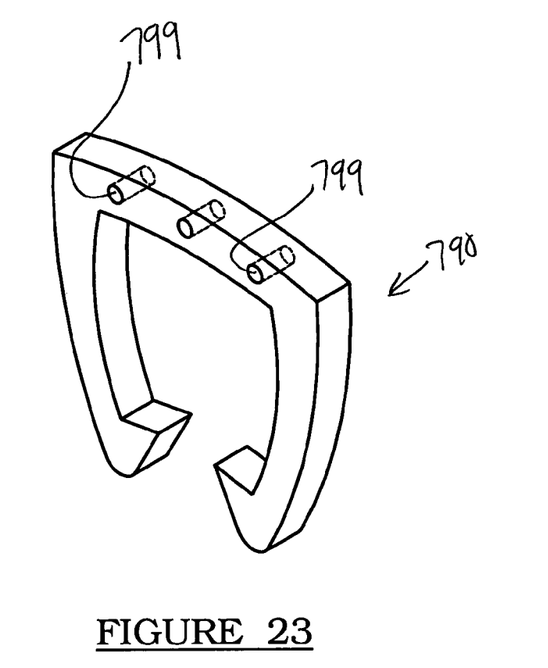
FIG. 23 is a perspective view of an alternate embodiment of the staple of FIG. 8.
Figure 24:
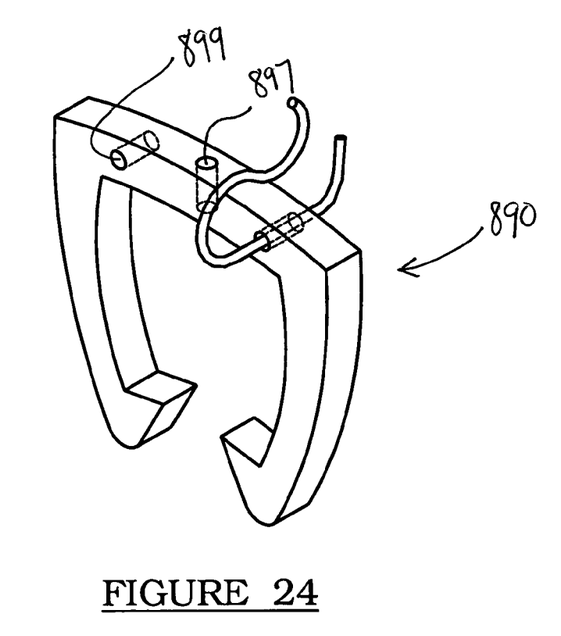
FIG. 24 is a perspective view of a further alternate embodiment of the staple of FIG. 8.

FIGS. 23 and 24 illustrate a further alternate embodiment of the staple of FIG. 8 wherein suture apertures are included to provide a suture attachment location for attachment of grafts to bone. FIG. 23 illustrates a staple 790 to include a suture aperture 799. FIG. 24 illustrates a staple 890 to include an alignment aperture 897 and a suture aperture 899. Alignment aperture 897 may be used with a guide wire to ensure proper alignment of staple 890 during installation onto an implant 10. Alignment aperture 897 may also be used as a suture aperture 899.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An implantation system comprising:
   an implant having an exterior threaded surface portion, said exterior threaded surface portion defining first and second channels said first channel having a longitudinal axis and a first locking surface;
   a driver, operable to be removably disposed within said first and second channels during the implantation of the implant, having a cutting portion and a driving portion, wherein the cutting portion is configured to form an implant engaging surface within a work material, and the driving portion is configured to drive the threaded portion into engagement with the implant engaging surface; and
   a generally u-shaped fastener having first and second members, wherein the first member is disposed within the first channel and configured to be fixed to the implant and the second member is outside the first channel, said first member defining a second locking surface engaged with the first locking surface thereby restricting linear movement of the u-shaped fastener in a first direction along the longitudinal axis of the first channel, said fastener and implant defining an aperture therebetween, said aperture being configured to fixably engage graft material and, wherein at least one of the implant or the fastener defines a graft engaging surface within the aperture, said graft engaging surface comprising a graft engaging member configured to engage the graft.

2. The system of claim 1 wherein the implant is a bone screw.

3. The system of claim 1 wherein the implant further comprises a generally cylindrical body, the body including a first end defining a top surface, a second end, a threaded outer surface and at least one channel, the channel extending from the top surface to the second end.

4. The system of claim 3 wherein the cutting portion includes a plurality of thread forming portions linearly spaced along the cutting portion, the cutting portion positioned within the first and second channels such that the implant can be threaded into an aperture formed within the work material as the cutting portion forms an internal threaded surface within the aperture.

5. The system of claim 1 wherein the work material is a bone.

6. The system of claim 1 wherein the implant is resorbable.

7. The system of claim 1 wherein the first and second channels define a pair of opposed channels.

8. An implantation system comprising:
   an implant having an exterior threaded surface which defines a pair of longitudinal channels, said longitudinal channels intersecting the exterior threaded surface;
   a driver having a cutting portion and a driving portion, wherein the cutting portion is configured to form an implant engaging surface within a work material, and the driving portion is configured to interface with a longitudinal channel of the implant to drive the threaded surface into engagement with the implant engaging surface, wherein the implant defines an anchor locking surface; and
   a staple configured to be at least partially disposed within the longitudinal channels having an upward locking surface, the upward locking surface engaged with the anchor locking surface so as to restrict translation of the staple in a first direction along a longitudinal axis of one channel of the pair of longitudinal channels.

9. The system of claim 8 further comprising a graft interposed between the staple and the implant.

10. A method of connecting an implant to a bone comprising:
    forming an implant engaging surface within a bone aperture by rotating a driver within the bone aperture;
    driving the implant into the bone aperture with the driver, wherein a threaded surface defining an arcuate groove of the implant engages the implant engaging surface, said implant further defining first and second longitudinal channels having first and second longitudinal axis within the threaded surface;
    inserting a staple into the first and second longitudinal channels defined within the threaded surface;
    fixably coupling the staple to the first and second longitudinal channels so as to restrict movement in a first direction along the first channel longitudinal axis, whereby the staple bindingly engages both the implant and a surface defining the bone aperture, said staple further intersecting the groove; and
    preventing rotation of the implant with respect to the bone with the staple in the first longitudinal channel.

11. The method of claim 10 further comprising forming a slot within the bone aperture.

12. The method of claim 11 wherein inserting the staple into the slot and inserting the staple into the channel are performed simultaneously.

13. The method of claim 10 wherein driving the implant into the bone aperture and rotating the driver are performed simultaneously.

14. The method of claim 10 wherein forming the implant engaging surface includes rotating the implant within the bone aperture.

15. The method of claim 10 further comprising forming a slot by translating a driver in a direction that is parallel to the axis of the bone aperture.

16. The method of claim 10 wherein driving the implant into the bone aperture forms a slot.

17. The method of claim 10 wherein driving the implant into the bone aperture includes linerally translating the implant.

18. The method of claim 10 wherein driving the implant includes threading a resorbable bone screw into the bone aperture.

19. The method of claim 10 wherein driving the implant includes linearly driving a resorbable bone screw into the bone aperture.

20. A method of connecting an implant to a bone comprising:
   forming an implant engaging surface within a bone aperture, said implant engaging surface defining a longitudinal channel;
   driving the implant into the bone aperture, wherein an exterior threaded surface defining an arcuate groove of the implant engages the implant engaging surface;
   inserting a staple along a first direction into a slot having a slot axis defined in the threaded surface, whereby the staple bindingly intersects the groove and engages both the implant and the bone aperture so as to resist rotation of the implant;
   engaging a locking surface of the staple with a surface of the implant so as to restrict linear movement of the staple in a second direction along the slot axis and with respect to the implant; and
   interposing a graft between the implant and a surface defining the staple.

21. The method of claim 20 wherein interposing the graft between the implant and the staple includes engaging the graft with a graft holding surface of the staple.

22. The method of claim 20 wherein interposing the graft between the implant and the staple includes engaging the graft with a graft holding face of the implant.

23. The method of claim 20 wherein inserting the staple into the slot includes engaging an anchor locking surface with a staple locking surface wherein the anchor locking surface defines at least a portion of a channel formed within the implant.

24. A method of driving an implant comprising:
   forming an aperture within a bone;
   defining a cutting surface accepting channel having a channel axis and a thread defining an arcuate groove in an exterior surface of the implant;
   coupling the implant to a driver so as to position a cutting surface within the channel;
   driving the implant into the aperture while the driver is in the channel;
   forming an implant engaging surface within the aperture;
   disposing a fastener within the channel in a first direction along the channel axis;
   coupling the fastener to the channel so as to prevent linear translation of the fastener along the channel axis in a second direction with respect to the implant;
   interrupting the arcuate groove and preventing rotation of the implant with respect to the aperture; and
   coupling soft tissue to the fastener.

25. The method of claim 24, wherein driving the implant and forming the aperture are performed simultaneously.

26. The method of claim 24, wherein driving the implant includes linearly translating the implant.

27. The method of claim 26, wherein driving the implant includes impacting the driver.

28. The method of claim 24, wherein driving the implant and forming the implant engaging surface are performed simultaneously.

29. The method of claim 24, wherein forming the implant engaging surface includes forming a threaded surface.

30. The method of claim 24, wherein driving the implant includes rotating the driver.

31. The method of claim 24, wherein forming the implant engaging surface includes forming the implant engaging surface with the implant.

32. The method of claim 24, wherein forming the implant engaging surface includes forming the implant engaging surface with the driver.

* * * * *